(12) United States Patent
Tao et al.

(10) Patent No.: US 10,428,364 B2
(45) Date of Patent: Oct. 1, 2019

(54) ENZYMATIC METHOD FOR PREPARING REBAUDIOSIDE M

(71) Applicant: PepsiCo, Inc., Purchase, NY (US)

(72) Inventors: Junhua Tao, Jiangsu (CN); Guoqing Li, Jiangsu (CN); Xiaoliang Liang, Jiangsu (CN); Andrew Tao, San Diego, CA (US)

(73) Assignee: PEPSICO, INC., Purchase, NY (US)

( * ) Notice: Subject to any disclaimer, the term of this patent is extended or adjusted under 35 U.S.C. 154(b) by 0 days.

(21) Appl. No.: 16/380,678

(22) Filed: Apr. 10, 2019

(65) Prior Publication Data
US 2019/0233866 A1 Aug. 1, 2019

Related U.S. Application Data

(62) Division of application No. 14/911,876, filed as application No. PCT/CN2013/084644 on Sep. 29, 2013, now Pat. No. 10,301,662.

(30) Foreign Application Priority Data

Aug. 14, 2013 (CN) .......................... 2013 1 0353500

(51) Int. Cl.
| | | |
|---|---|---|
| C12P 19/58 | (2006.01) | |
| C12N 1/20 | (2006.01) | |
| C12N 15/00 | (2006.01) | |
| C07H 21/04 | (2006.01) | |
| C12N 9/10 | (2006.01) | |
| C12P 19/56 | (2006.01) | |
| A23L 27/30 | (2016.01) | |
| C12P 19/18 | (2006.01) | |

(52) U.S. Cl.
CPC ............... *C12P 19/56* (2013.01); *A23L 27/36* (2016.08); *C12N 9/1051* (2013.01); *C12P 19/18* (2013.01); *C12Y 204/01017* (2013.01); *A23V 2002/00* (2013.01)

(58) Field of Classification Search
None
See application file for complete search history.

(56) References Cited

U.S. PATENT DOCUMENTS

| | | |
|---|---|---|
| 9,752,174 B2 | 9/2017 | Markosyan |
| 10,301,662 B2 | 5/2019 | Tao et al. |
| 2010/0099857 A1 | 4/2010 | Evans |
| 2011/0218161 A1 | 9/2011 | Han et al. |
| 2013/0171328 A1 | 7/2013 | Kishore et al. |
| 2016/0186225 A1 | 6/2016 | Mikkelsen |
| 2017/0211113 A1 | 7/2017 | Tao et al. |

FOREIGN PATENT DOCUMENTS

| | | |
|---|---|---|
| CA | 2 913 252 A1 | 12/2014 |
| CN | 103031283 A | 4/2013 |
| CN | 103088041 A | 5/2013 |
| CN | 103179850 A | 6/2013 |
| JP | 2010-538621 | 12/2010 |
| JP | 2012-504552 A | 2/2012 |
| RU | 2 596 190 C9 | 10/2016 |
| WO | WO 2010/038911 A1 | 4/2010 |
| WO | WO 2011046423 A1 | 4/2011 |
| WO | WO 2011/153378 A1 | 12/2011 |
| WO | WO 2012/103074 A2 | 8/2012 |
| WO | WO 2013/022989 A2 | 2/2013 |
| WO | WO 2013/096420 A1 | 6/2013 |
| WO | WO 2013/110673 A1 | 8/2013 |
| WO | WO 2013/176738 A1 | 11/2013 |
| WO | WO 2014/086890 A1 | 6/2014 |
| WO | WO 2014/122227 A2 | 8/2014 |
| WO | WO 2015/021690 A1 | 2/2015 |
| WO | WO 2016/196345 A1 | 12/2016 |

OTHER PUBLICATIONS

GenBank, "UDP-glycosyltransferase 76G1 [Stevia rebaudiana]," Accession No. AAR06912.1, accessed at http://www.ncbi.nlm.nih.gov/protein/AAR06912, accessed on May 26, 2016, 2 pages.

GenBank, "Os03g0702000 [*Oryza sativa* Japonica Group]," Accession No. NP_001051007.2, accessed at http://www.ncbi.nlm.nih.gov/protein/NP_001051007.2?report=genpept, accessed on May 26, 2016, 4 pages.

Masada, S., et al., "An efficient chemoenzymatic production of small molecule glucosides with in situ UDP-glucose recycling," *FEBS Letters* 581(13):2562-2566, Elsevier B.V., Netherlands (2007).

Ohta, M., et al., "Characterization of Novel Steviol Glycosides from Leaves of *Stevia rebaudiana* Morita," *J. Appl. Glycosci.* 57(3):199-209, The Japanese Society of Applied Glycoscience, Japan (2010).

Wang, Q.J., et al., "*Saccharomyces cerevisiae* surface expression of sucrose synthase," China resources biotechnology and enzyme engineering symposium proceedings (2005).

Wölwer-Rieck, U., "The leaves of Stevia rebaudiana (Bertoni), their constituents and the analyses thereof: a review," *J Agric Food Chem.* 60(4):886-895, American Chemical Society, United States (2012).

International Preliminary Report on Patentability for International Application No. PCT/CN2013/084644, The International Bureau of WIPO, Switzerland, dated Feb. 16, 2016, 7 pages.

International Search Report and Written Opinion for International Application No. PCT/CN2013/084644, State Intellectual Property Office of the P.R. China, Beijing, China, dated May 14, 2014, 12 pages.

English translation of International Search Report and Written Opinion for International Application No. PCT/CN2013/084644, State Intellectual Property Office of the P.R. China, Beijing, China, dated May 14, 2014, 12 pages.

(Continued)

*Primary Examiner* — Yong D Pak
(74) *Attorney, Agent, or Firm* — Sterne, Kessler, Goldstein & Fox P.L.L.C.

(57) ABSTRACT

Provided is a method for preparing rebaudioside M by using an enzyme method. In the method, rebaudioside A or rebaudioside D is used as a substrate; and in the existence of a glucosyl donor, rebaudioside M is generated by means of reaction of the substrate under the catalysis of UDP-glucosyl transferase and/or recombinant cells containing the UDP-glucosyl transferase.

16 Claims, 1 Drawing Sheet

Specification includes a Sequence Listing.

(56) References Cited

OTHER PUBLICATIONS

International Preliminary Report on Patentability for International Application No. PCT/CN2014/071715, The International Bureau of WIPO, Geneva, Switzerland, dated Aug. 2, 2016, 5 pages.
International Search Report and Written Opinion for International Application No. PCT/CN2014/071715, State Intellectual Property Office of the P.R. China, dated Oct. 22, 2014, 9 pages.
English translation of International Search Report and Written Opinion for International Application No. PCT/CN2014/071715, State Intellectual Property Office of the P.R. China, dated Oct. 22, 2014, 9 pages.
Co-pending Application, U.S. Appl. No. 15/114,250, inventors Tao, J., et al., I.A. filed Jan. 28, 2014 (Not Published).
Extended European Search Report for EP Application No. 13891561.6, Munich, Germany, dated Mar. 13, 2017, 7 pages.
Pearson, W.R., "An Introduction to Sequence Similarity ("Homology") Searching," *Curr Protoc Bioinformatic*, Author Manuscript, Jun. 3, Wiley, USA (2013).
Office Action dated Dec. 1, 2017, in U.S. Appl. No. 15/114,250, Tao, J. et al., filed Jul. 26, 2016, 7 pages.
Whisstock et al. Quarterly Reviews of Biophysics, 2003, "Prediction of protein function from protein sequence and structure", 36(3): 307-340.
Witkowski et al. Conversion of a beta-ketoacyl synthase to a malonyl decarboxylase by replacement of the active-site cysteine with glutamine, Biochemistry. Sep. 7, 1999;38(36): 11643-50.
Chen, R.R., Permeability issues in whole-cell bioprocesses and cellular membrane engineering, Appl Microbial Biotechnol (2007) 74:730-738.
UniProtKB-F2DT21 (F2DT21_HORVD), May 31, 2011, accessed at http://www.uniprot.org/uniprot/F2DT21, 4 pages.
Co-pending Application, U.S. Appl. No. 15/932,218, inventors Anderson, A., et al., filed Aug. 19, 2016 (Not Published).
Co-pending Application, U.S. Appl. No. 15/740,572, inventors Du, H., et al., filed Aug. 21, 2015 (Not Published).
Son, M.H., et al., "Production of Flavonoid O-Glucoside Using Sucrose Synthase and Flavonoid O-Glucosyltransferase Fusion Protein," J. Microbiol. Biotechnol. 19(7):709-12, Springer Nature, Switzerland (2009).
Mohamed, A.A. et al., "UDP-dependent glycosyltransferases involved in the biosynthesis of steviol glycosides," J Plant Physiol. 168(10):1136-41, Elsevier, Netherlands (2011).
Branden, C. et al., "Prediction, Engineering, and Design of Protein Structures," Introduction to Protein Structure, Garland Publishing Inc., New York, p. 247, 1991.
Studer, R.A. et al., "Residue mutations and their impact on protein structure and function:detecting beneficial and pathogenic changes," Biochem. J. 449:581-594, Biochemical Society, England (2013).
Office Action dated Jan. 31, 2019, in U.S. Appl. No. 15/114,250, inventors Tao, et al., filed Jul. 26, 2016, 19 pages.
Office Action dated Sep. 12, 2018, in U.S. Appl. No. 15/114,250, inventors Tao, et al., filed Jul. 26, 2016, 19 pages, 27 pages.

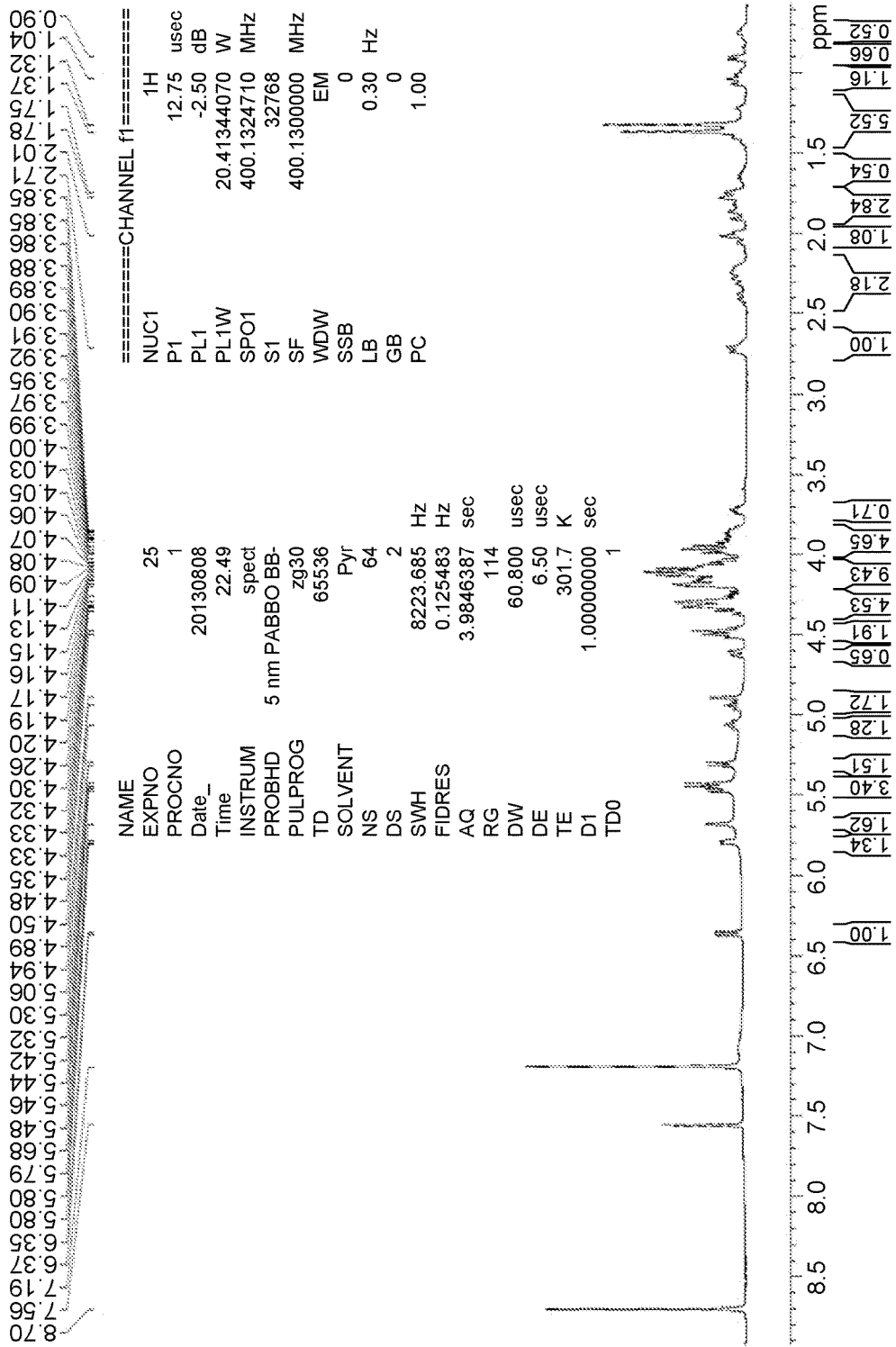

SEQUENCE LISTING

```
<160> NUMBER OF SEQ ID NOS: 4

<210> SEQ ID NO 1
<211> LENGTH: 1377
<212> TYPE: DNA
<213> ORGANISM: Artificial Sequence
<220> FEATURE:
<223> OTHER INFORMATION: Synthesized nucleotide sequence

<400> SEQUENCE: 1
atggaaaaca aaaccgaaac cacggtacgc cgtcgtcgtc gtatcatcct cttcccggtt     60
ccgtttcagg gtcacatcaa cccgatcctt cagttggcaa acgtactgta ctctaaaggt    120
tttagcatca ccattttca cactaacttt aacaaaccga aacctctaa ctatccgcac      180 ttcactttcc gcttcatcct ggacaacgac ccgcaagatg agcgcattag caacctgccg    240
acccatggcc cgctggcagg catgcgcatc cctatcatca tgaacacgg cgctgacgaa     300 ctgcgtcgtg agctggaact cctgatgctg gcttctgaag aagacgagga agtgtcttgc    360
ctgattacag acgctctctg gtactttgct cagagcgtgg cggactctct gaacctgcgc    420
cgtctggttc ttatgacttc ttccttgttt aatttccatg cgcatgtctc tctgccgcag    480
ttcgacgagc tgggctacct ggacccggat gacaaaactc gcctggagga acaggcatct    540
ggcttcccga tgctgaaagt aaaagatatc aaaagcgcat actccaattg gcagatcctg    600
aaagagattc tgggcaaaat gatcaagcag actaaagcat ccagcggcgt tatctggaac    660 tccttttaaag agctggagga aagcgaactg gaaaccgtga tccgtgaaat cccggcaccg    720
tcgttcctga ttcctctgcc taaacatctg accgcctcct cttcttctct gctggatcac    780
```

```
gatcgcaccg tttccagtg ctggatcag caaccgccga gttctgtgct gtatgtttct    840
ttcggctcga cgagtgaggt tgacgaaaaa gacttcctgg aaatcgcacg cggcctggtt    900
gactctaaac agagctttct gtgggttgta cgtccgggtt cgtgaaggg cagcacctgg    960 gttgaaccgc tgccgacgg cttttgggc gaacgcggcc gtatcgtaaa atgggtaccg    1020
cagcaggagg tactggcaca cggcgcaatt ggggcgttct ggactcactc cggctggaac    1080
tccactctgg aatccgtatg cgaaggcgtt cctatgattt tcagcgactt cggcctggat    1140
cagccgctga acgcacgcta tgtcagac gttctgaaag tcggtgtgta tctggagaac    1200
gggtgggagc gtggcgaaat tgccaacgcg atccgtcgtg ttatggtgga tgaagaaggc    1260
gaatacatcc gtcagaacgc tcgtgtcctt aaacagaaag ctgacgtgag cctgatgaaa    1320
ggtggctcta gctacgaatc gctggagtcc ctggtttctt acatctcgtc gctgtaa    1377
```

```
<210> SEQ ID NO 2
<211> LENGTH: 458
<212> TYPE: PRT
<213> ORGANISM: Artificial Sequence
<220> FEATURE:
<223> OTHER INFORMATION: Synthesized protein sequence

<400> SEQUENCE: 2

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255
```

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 3
<211> LENGTH: 1389
<212> TYPE: DNA
<213> ORGANISM: Artificial Sequence
<220> FEATURE:
<223> OTHER INFORMATION: Synthesized nucleotide sequence

<400> SEQUENCE: 3
atggacagcg gttactcttc tagctatgct gcggcagccg gtatgcacgt agttatttgt      60
ccgtggctcg ctttcggtca cctcctgccg tgcctggacc tggcgcagcg cctggcatct     120
cgtggtcacc gtgtcagttt cgttagcacg ccgcgtaaca tctcacgtct gccgccggtc     180
cgtccggctc tggccccgct ggttgcgttc gttgcgctac ctctgccgcg cgttgaaggc     240
ttaccggatg gcgcagagtc taccaacgac gtgccgcacg atcgcccgga tatggttgaa     300
ctccaccgcc gtgcatttga cggtctggca gctccgttct ccgaatttct gggtaccgcg     360
tgtgccgact gggtcatcgt agacgtattc caccactggg cagctgcagc ggctttagaa     420
cacaaagtac cgtgcgcaat gatgctgctg ggctctgctc acatgatcgc gtctattgcc     480
gaccgtcgtc tggaacgtgc agagaccgaa tctccagcgg cagccggtca gggccgtcct     540
gcagctgctc cgaccttcga agttgctcgt atgaagctca tccgcactaa aggttcttcc     600
ggtatgtcac tggcagagcg tttctcgctg acgctctccc gtagcagcct ggttgtgggg     660
cgctcctgcg tggaattcga accggaaact gtgccgctac tgtctaccct gcgtggcaag     720
ccgatcactt ttctgggtct catgccgcca ctgcacgaag tcgccgcgca agacggtgaa     780
gatgctacgg ttcgttggtt ggacgcccag ccggctaaaa gcgtcgtgta cgtagctctg     840
ggcagtgaag ttccattggg tgtcgagaaa gtgcatgaac tggctttggg tctggagctg     900

```
gctggcaccc gtttcctctg ggcactgcgt aagccgactg gtgtgtctga tgctgacctt    960
ctgccggctg gtttcgaaga acgtacccgt ggtcgcggcg tagtggcaac ccgctgggta   1020
ccgcagatgt ccatcctggc acacgctgct gttggcgcgt ttcttaccca ctgcgggtgg   1080
aactctacaa tcgaaggcct gatgttcggc atcctctga ttatgctgcc aatcttcggt    1140
gatcagggtc cgaacgctcg tctgatcgaa gccaaaaacg ccggcttaca agtcgcacgc   1200
aacgacggcg atggttcttt cgatcgtgaa ggtgttgcgg cagctatccg tgcagtggct   1260
gtagaagaag agtcgagcaa agtgttccag gcaaaagcca aaaagctgca ggaaatcgtt   1320
gcggacatgg cgtgccacga acgttacatc gatggcttta ccagcagct gcgctcctac    1380 aaagattaa                                                            1389
```

<210> SEQ ID NO 4
<211> LENGTH: 462
<212> TYPE: PRT
<213> ORGANISM: Artificial Sequence
<220> FEATURE:
<223> OTHER INFORMATION: Synthesized protein sequence

<400> SEQUENCE: 4

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270
```

-continued

```
Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305             310                 315                 320

Leu Pro Ala Gly Phe Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
    370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
        450                 455                 460
```

ENZYMATIC METHOD FOR PREPARING REBAUDIOSIDE M

REFERENCE TO SEQUENCE LISTING SUBMITTED ELECTRONICALLY

The content of the electronically submitted sequence listing (Name: Sequence Listing.txt; Size: 12,448 bytes; and Date of Creation: Aug. 11, 2017) is herein incorporated by reference in its entirety.

TECHNICAL FIELD

The present invention relates to a method for preparing rebaudioside M, and in particular to a biological method for preparing rebaudioside M.

BACKGROUND ART

Sweetening agents are a class of food additives that have wide applications in the production of food products, beverages and candy. They may be added in the production process of a food product, or alternatively may be used through appropriate dilution as a surrogate for sucrose during household baking. Sweetening agents include natural sweetening agents, for example, sucrose, high fructose corn syrup, honey, etc., and artificial sweetening agents, for example, aspartame, saccharine, etc. Steviosides are a class of natural sweetening agents extracted from the plant *Stevia rebaudiana*, and are widely used in food products and beverages at present. The extract of *Stevia rebaudiana* contains a variety of steviosides comprising rebaudioside. Naturally extracted steviosides have great differences in ingredients across different batches, and need subsequent purification. A current commercialized product rebaudioside A comprises some other steviosides, for example, rebaudiosides C, D and F, etc. Stevioside prepared by an extraction method generally further has some impurities mixed therein, which will cause a certain influence on the application field thereof. Rebaudioside M has advantages over rebaudioside A, but has a very low content in leaves of *Stevia rebaudiana*, and is detected only in a *Stevia rebaudiana* Morita plant (2010, J. Appl. Glycosci., 57, 199-209). There is yet to be any commercialized production of rebaudioside M at present.

SUMMARY OF THE INVENTION

A technical issue to be solved in the present invention is to provide a method for preparing rebaudioside M by an enzyme method in order to overcome drawbacks in the prior art. This method can produce a high-purity rebaudioside M product at a lower cost within a shorter period of time.

In order to solve the above technical issue, the present invention employs a technical solution as follows: a method for preparing rebaudioside M by an enzyme method. In the method, rebaudioside A or rebaudioside D is used as a substrate; and in the existence of a glucosyl donor, rebaudioside M is generated by means of reaction of the substrate under the catalysis of UDP-glucosyl transferase and/or recombinant cells containing the UDP-glucosyl transferase.

According to the present invention, the glucosyl donor may be UDP-glucose, or a UDP-glucose regeneration system composed of sucrose, sucrose synthetase and UDP (2007, FEBS Letters, 581, 2562-2566), and preferably the UDP-glucose regeneration system composed of sucrose, sucrose synthetase and UDP. UDP glucose is more costly, and the employment of the UDP-glucose regeneration system can substantially reduce the cost.

According to the present invention, the UDP-glucosyl transferase (i.e., uridine diphosphoglucosyl transferase, abbreviated as UGT) is known. Preferably, the UDP-glucosyl transferase employed in the present invention is UGT-A from *Stevia rebaudiana* and/or UGT-B from *Oryza sativa*.

The amino acid sequence of UGT-A may have at least 60% identity to sequence 2. Preferably, the amino acid sequence of UGT-A has at least 70% identity to sequence 2. Further preferably, the amino acid sequence of UGT-A has at least 80% identity to sequence 2. Most preferably, the amino acid sequence of UGT-A has at least 90% identity to sequence 2. According to one particular aspect, the amino acid sequence of UGT-A is completely identical to sequence 2.

The amino acid sequence of UGT-B may have at least 60% identity to sequence 4. More preferably, the amino acid sequence of UGT-B has at least 70% identity to sequence 4. Further preferably, the amino acid sequence of UGT-B has at least 80% identity to sequence 4. Most preferably, the amino acid sequence of UGT-B has at least 90% identity to sequence 4. According to one particular aspect, the amino acid sequence of UGT-B is completely identical to sequence 4.

According to the present invention, the reaction may be carried out in an aqueous phase system at a temperature from 4° C. to 50° C. and a pH value from 5.0 to 9.0. Preferably, the reaction is carried out in an aqueous phase system at a temperature from 25° C. to 35° C. and a pH value from 6.5 to 7.5.

More preferably, the reaction is carried out at a temperature of 30° C.

More preferably, the reaction is carried out at a pH value of 7.0.

According to one particular preferred aspect, the reaction is carried out in a phosphate buffer at pH 7.

According to the present invention, when the catalysis is carried out employing recombinant cells containing the UDP-glucosyl transferase, the reaction may be carried out in the presence of a cellular permeating agent. Preferably, the cellular permeating agent is toluene, at a concentration that may be from 1% to 3% according to the ratio by volume in the whole reaction system. More preferably, toluene has a concentration of 2% according to the ratio by volume.

According to the present invention, the recombinant cells may be and are preferably microbial cells, where the microorganisms may be and are preferably *Escherichia coli, Saccharomyces cerevisiae* or *Pichia pastoris*, and the like. According to one particular and preferred aspect, the preparation method is implemented as follows: all the raw materials employed in the reaction are added into a reaction kettle, mixed uniformly, then placed at a set temperature, and stirred for reaction. After completion of the reaction, a rebaudioside M product meeting the use requirements can be obtained through purification treatment. In one particular purification method, a rebaudioside M product with purity as high as 95% can be obtained according to the purification method through aftertreatment including separation by resin.

According to a particular aspect of the present invention, the substrate is rebaudioside A, and the UDP-glucosyl transferase is a mixture of UGT-A from *Stevia rebaudiana* and UGT-B from *Oryza sativa*, where the amino acid sequence of UGT-A from *Stevia rebaudiana* has at least 80% identity to sequence 2, and the amino acid sequence of UGT-B from *Oryza sativa* has at least 80% identity to sequence 4. Preferably, in the mixture, UGT-A from *Stevia rebaudiana* and UGT-B from *Oryza sativa* have a ratio by weight that is 1:0.8 to 1.2, for example, that may be 1:1.

According to yet another particular aspect of the present invention, the substrate is rebaudioside D, and the UDP-glucosyl transferase is UGT-A from *Stevia rebaudiana*, where the amino acid sequence of UGT-A from *Stevia rebaudiana* has at least 80% identity to sequence 2.

As a result of implementation of the above technical solutions, the present invention has the following advantages as compared with the prior art.

The method for preparing rebaudioside M by an enzyme method provided in the present invention has an important application value. Because the growth rate of microorganisms is far faster than that of plants, by employing the preparation method according to the present invention, the production cost can be reduced dramatically, the production cycle can be shortened, and the competitive power of the product can be improved greatly. In addition, stevioside has a low content in plants, and has relatively more steviosides of different structures, so that it is extremely difficult to extract purer products. Whereas the employment of the synthetic method by using an enzyme method according to the present invention is capable of providing products with higher purity, which will further expand the application field thereof. As compared with the technique for extracting rebaudioside M from leaves of *Stevia rebaudiana*, the method according to the present invention possesses a significantly shortened production cycle, improved productive capacity, lower cost, and can provide products with higher purity, and thus can be used more economically in industries of food products and beverages.

BRIEF DESCRIPTION OF THE DRAWINGS

FIG. 1 is a proton magnetic spectrum diagram of a product obtained in Example 5 of the present invention.

DETAILED DESCRIPTION OF THE PREFERRED EMBODIMENTS

The following rebaudioside A, rebaudioside D, and rebaudioside M are abbreviated respectively as Reb A, Reb D and Reb M, with structural formulae respectively referring to Formulae I, II, and III.

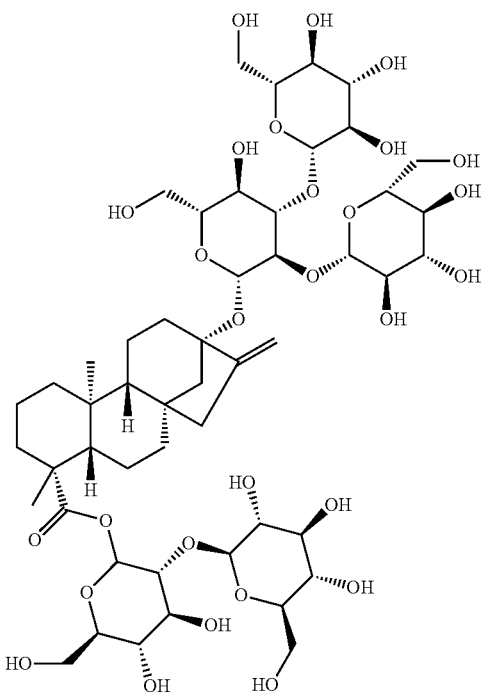

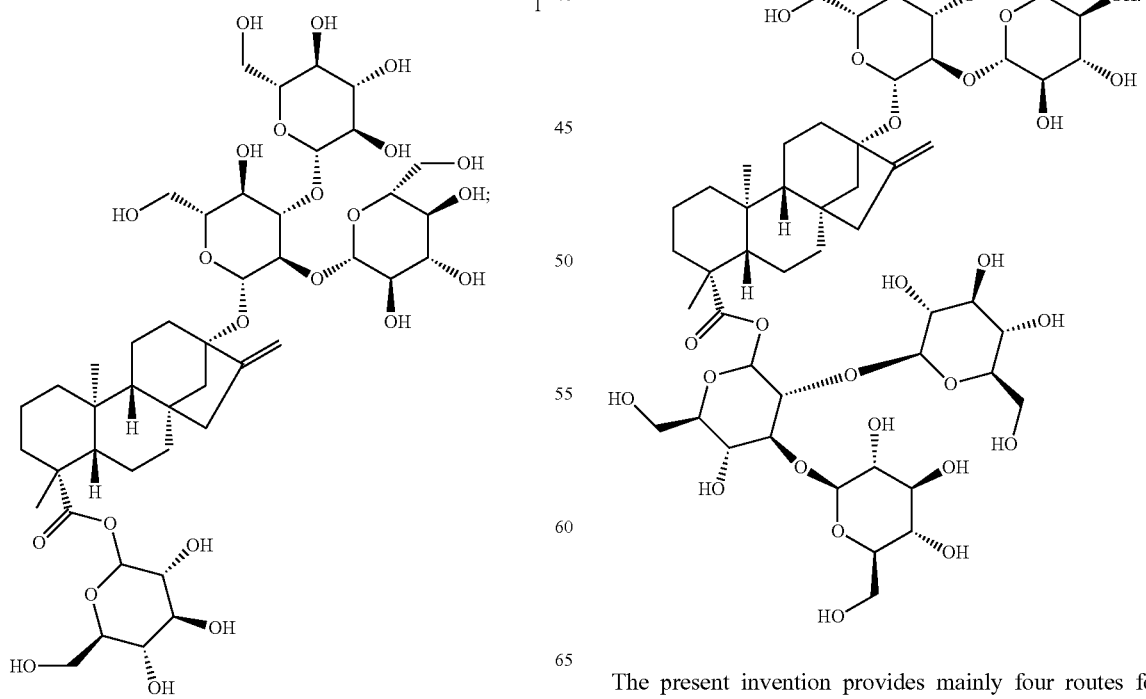

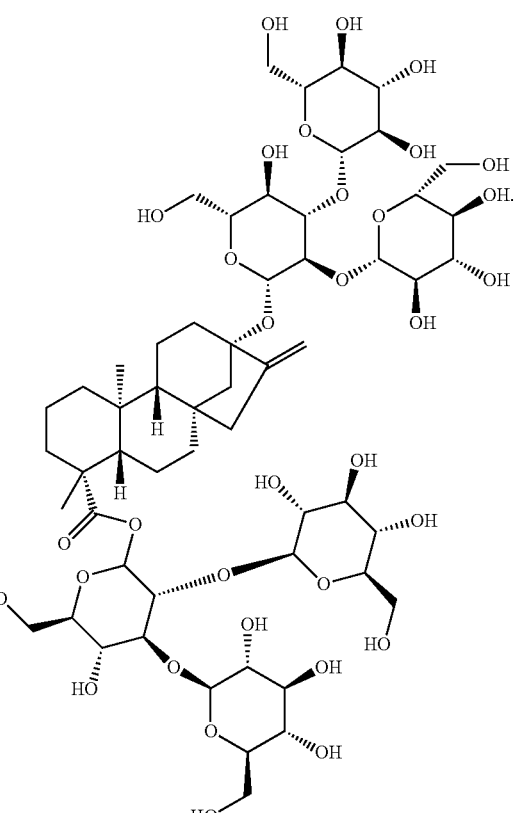

The present invention provides mainly four routes for synthesizing Reb M:

Route 1:

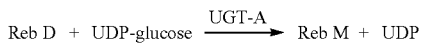

Route 2:

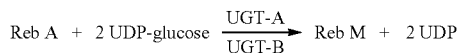

Route 3:

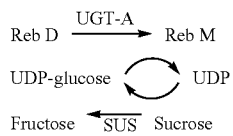

Route 4:

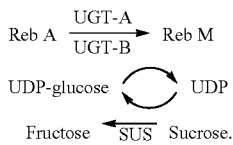

According to the present invention, employed UGT-A or UGT-B may occur in a form of a lyophilized enzyme powder, or present in recombinant cells.

UGT-A or UGT-B is obtained by a method as follows:

Recombinant *Escherichia coli* (or other microbial bacteria) expression strains of UGT-A or UGT-B are obtained by utilizing molecular cloning techniques and genetic engineering techniques. Then the recombinant *Escherichia coli* are fermented, to prepare recombinant cells containing UGT-A or UGT-B, or to prepare lyophilized powders of UGT-A or UGT-B.

The above molecular cloning techniques and genetic engineering techniques are all known. Molecular cloning techniques may be seen in *Molecular Cloning: A Laboratory Manual*. 3rd Edition, by J. Sambrook, 2005.

Expression steps for constructing the recombinant strains of the present invention by employing the genetic engineering technique are as follows:

(1) (according to sequence 1 and sequence 2, or according to sequence 3 and sequence 4,) required gene fragments are genetically synthesized, pUC57 vectors are ligated therein, and NdeI and BamHI enzyme cutting sites are added on both ends respectively;

(2) through double enzyme digestion and the ligation, each of the gene fragments is inserted into the corresponding enzyme cutting sites of the expression vector pET30a, to allow each of the genes to be subjected to the control of the T7 promoter; and (3) recombinant plasmids are transformed into *Escherichia coli* BL21 (DE3), and target proteins are induced to express by utilizing IPTG, so as to obtain recombinant *Escherichia coli* expression strains of UGT-A or UGT-B.

The recombinant cells containing UGT-A or UGT-B, or the lyophilized powders of UGT-A or UGT-B are prepared by utilizing the recombinant *Escherichia coli* expression strains containing UGT-A or UGT-B, by steps as follows:

The recombinant *Escherichia coli* expression strains containing UGT-A or UGT-B are inoculated into 4 ml of a liquid LB medium at a proportion of 1%, and shaken (200 rpm) at 37° C. for culturing overnight. The culture that has experienced overnight culturing is transferred to 50 ml of the liquid LB medium in an inoculum size of 1%. The culture medium is shaken (200 rpm) at 37° C. for culturing to an OD600 value up to 0.6-0.8. IPTG at a final concentration of 0.4 mM is added therein, and the mixture is shaken at 20° C. for culturing overnight. After completion of the induction, cells are collected by centrifugation (8,000 rpm, 10 min). The cells are resuspended using 5 ml of a 2 mmol/L phosphate buffer (pH 7.0) to obtain recombinant cells, or further ruptured ultrasonically in an ice bath to obtain a lyophilized powder by centrifuging the ruptured liquid (8,000 rpm, 10 min), collecting the supernatant, and lyophilizing for 24 hours.

The present invention will be described below in more details in conjunction with particular examples.

Example 1: Preparation of Recombinant *Escherichia coli* Cells Containing UGT-A

According to sequence 1 and sequence 2, UGT-A gene fragments were genetically synthesized, NdeI and BamHI enzyme cutting sites were added on both ends respectively, and pUC57 vectors (Suzhou Genewiz Biotech Co., Ltd.) were ligated therein. The UGT gene fragments were subjected to enzyme digestion with restriction endonucleases NdeI and BamHI. Purified fragments were recovered. T4 ligase was added therein, and the fragments were ligated into corresponding enzyme cutting sites of pET30a, to transform the BL21 (DE3) strains.

The UGT strains were inoculated into 4 ml of a liquid LB medium at a proportion of 1%, and shaken (200 rpm) at 37° C. for culturing overnight. The culture that had experienced overnight culturing was transferred to 50 ml of the liquid LB medium in an inoculum size of 1%. The culture medium was shaken (200 rpm) at 37° C. for culturing to an $OD_{600}$ value up to 0.6-0.8. IPTG at a final concentration of 0.4 mM was added therein, and the mixture was shaken at 20° C. for culturing overnight. After completion of the induction, cells were collected by centrifugation (8,000 rpm, 10 min). The cells were resuspended using 5 ml of a 2 mmol/L phosphate buffer (pH 7.0) to obtain recombinant cells containing UGT-A for use in the catalysis.

Example 2: Preparation of Lyophilized UGT-A Powder

The recombinant cells of UGT-A prepared in Example 1 were ruptured ultrasonically in an ice bath, to obtain a lyophilized powder of UGT-A by centrifuging the ruptured liquid (8,000 rpm, 10 min), collecting the supernatant, and lyophilizing for 24 hours.

Example 3: Preparation of Recombinant *Escherichia coli* Cells Containing UGT-B

According to sequence 3 and sequence 4, UGT-B gene fragments were genetically synthesized, NdeI and BamHI enzyme cutting sites were added on both ends respectively, and pUC57 vectors (Suzhou Genewiz Biotech Co., Ltd.) were ligated therein. The UGT gene fragments were subjected to enzyme digestion with restriction endonucleases NdeI and BamHI. Purified fragments were recovered. T4 ligase was added therein, and the fragments were ligated into corresponding enzyme cutting sites of pET30a, to transform the BL21 (DE3) strains.

The UGT strains were inoculated into 4 ml of a liquid LB medium at a proportion of 1%, and shaken (200 rpm) at 37° C. for culturing overnight. The culture that had experienced overnight culturing was transferred to 50 ml of the liquid LB medium in an inoculum size of 1%. The culture medium was shaken (200 rpm) at 37° C. for culturing to an $OD_{600}$ value up to 0.6-0.8. IPTG at a final concentration of 0.4 mM was added therein, and the mixture was shaken at 20° C. for culturing overnight. After completion of the induction, cells were collected by centrifugation (8,000 rpm, 10 min). The cells were resuspended using 5 ml of a 2 mmol/L phosphate buffer (pH 7.0) to obtain recombinant cells containing UGT-B for use in the catalysis.

Example 4: Preparation of Lyophilized UGT-B Powder

The recombinant cells of UGT-B prepared in Example 3 were ruptured ultrasonically in an ice bath, to obtain a lyophilized powder of UGT-B by centrifuging the ruptured liquid (8,000 rpm, 10 min), collecting the supernatant, and lyophilizing for 24 hours.

Example 5: Synthesis of Reb M by an Enzyme Method with Reb D as a Substrate (Route 1)

In this example, the lyophilized UGT-A powder prepared according to the method in Example 2 was used in the catalytic synthesis of Reb M.

150 mL of a 0.05 mol/L phosphate buffer (pH 7.0), 0.255 g of UDP glucose, 0.17 g of Reb D, and 1.5 g of the lyophilized UGT-A powder were added successively into the reaction system, mixed uniformly, then placed in a water bath at 30° C., and stirred at 160 rpm to carry out reaction for 2 hours. After completion of the reaction, 500 μl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%:80%; flow rate: 1.0 mL/min; column temperature: 25° C.). A conversion rate of Reb D was more than 40%. 0.054 g of Reb M with a purity greater than 95% was obtained after purification by aftertreatments, such as, separation by silica gel resin, crystallization, etc.

Example 6: Synthesis of Reb M by an Enzyme Method with Reb a as a Substrate (Route 2)

In this example, the lyophilized UGT-A powder prepared according to the method in Example 2 and the lyophilized UGT-B powder prepared according to the method in Example 4 were used in the catalytic synthesis of Reb M.

150 mL of a 0.05 mol/L phosphate buffer (pH 7.0), 0.51 g of UDP glucose, 0.145 g of Reb A, and 1.5 g each of lyophilized powders of UGT-A and UGT-B were added successively into the reaction system, mixed uniformly, then placed in a water bath at 30° C., and stirred at 160 rpm to carry out reaction for 2 hours. After completion of the reaction, 500 μl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%:80%; flow rate: 1.0 mL/min; column temperature: 25° C.). A conversion rate of Reb A was more than 40%. 0.05 g of Reb M with a purity greater than 95% was obtained after purification by after treatments, such as, separation by silica gel resin, crystallization, etc.

Example 7: Synthesis of Reb M by an Enzyme Method with Reb D as a Substrate (Route 3)

In this Example, a UDP-glucose regeneration system composed of sucrose, sucrose synthetase (AtSUS1 for short hereafter) from *Arabidopsis thaliana*, and UDP was used as a glucosyl donor.

150 mL of a 0.05 mol/L phosphate buffer (pH 7.0), 0.182 g of UDP, 51.3 g of sucrose, 0.17 g of Reb D, 1.5 g of the lyophilized UGT-A powder and 0.5 g of the lyophilized AtSUS1 powder were added successively into the reaction system, mixed uniformly, then placed in a water bath at 30° C., and stirred at 160 rpm to carry out reaction for 2 hours. After completion of the reaction, 500 μl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%:80%; flow rate: 1.0 mL/min; column temperature: 25° C.). A conversion rate of Reb D was more than 80%. 0.11 g of Reb M with a purity greater than 95% was obtained after purification by aftertreatments, such as, separation by silica gel resin, crystallization, etc.

Example 8: Synthesis of Reb M by an Enzyme Method with Reb a as a Substrate (Route 4)

In this Example, a UDP-glucose regeneration system composed of sucrose, sucrose synthetase (referred to as AtSUS1 hereafter) from *Arabidopsis thaliana*, and UDP was used as a glucosyl donor.

150 mL of a 0.05 mol/L phosphate buffer (pH 7.0), 0,364 g of UDP, 51.3 g of sucrose, 0.145 g of Reb A, 1.5 g each of UGT-A and UGT-B, and 0.5 g of the lyophilized AtSUS1 powder were added successively into the reaction system, mixed uniformly, then placed in a water bath at 30° C., and stirred at 160 rpm to carry out reaction for 2 hours. After completion of the reaction, 500 μl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%: 80%; flow rate: 1.0 mL/min; column temperature: 25° C.). A conversion rate of Reb A was more than 80%. 0.108 g of Reb M with a purity greater than 95% was obtained after purification by aftertreatments, such as, separation by silica gel resin, crystallization, etc.

Example 9: Synthesis of Reb M by Whole Cell Catalytic Synthesis with Reb D as a Substrate In this example, the recombinant cells containing UGT-A prepared according to the method in Example 1 was used in the catalytic synthesis of Reb M.

150 mL of a 0.05 mol/L phosphate buffer (pH 7.0), 0.255 g of UDP glucose, 3 mL of toluene, 0.17 g of Reb D, and 10 g of recombinant cells containing UGT-A were added successively into the reaction system, mixed uniformly, then placed in a water bath at 30° C., and stirred at 160 rpm to carry out reaction for 2 hours. After completion of the reaction, 500 µl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%: 80%; flow rate: 1.0 mL/min; column temperature: 25° C.). A conversion rate of Reb D was more than 40%. 0.052 g of Reb M with a purity greater than 95% was obtained after purification by aftertreatments, such as, centrifugation, separation by passing the supernatant through silica gel resin, crystallization, etc.

Example 10: Synthesis of Reb M by Whole Cell Catalytic Synthesis with Reb a as a Substrate 150 mL of a 0.05 mol/L phosphate buffer (pH 7.0), 0.51 g of UDP glucose, 3 mL of toluene, 0.145 g of Reb A, and 10 g of whole cells containing UGT-A and UGT-B at the same time were added successively into the reaction system, mixed uniformly, then placed in a water bath at 30° C., and stirred at 160 rpm to carry out reaction for 2 hours. After completion of the reaction, 500 µl of the reaction solution was taken and added into an equal volume of anhydrous methanol and mixed uniformly. The mixture was centrifuged for 10 min at 8,000 rpm. The supernatant was taken and passed through a filter membrane, followed by detection using high performance liquid chromatography (chromatographic condition: chromatographic column: Agilent eclipse sb-C18 4.6×250 mm; detection wavelength: 210 nm; mobile phase: 1% formic acid aqueous solution:methanol=20%: 80%; flow rate: 1.0 mL/min; column temperature: 25° C.). A conversion rate of Reb A was more than 40%. 0.05 g of Reb M with a purity greater than 95% was obtained after purification by aftertreatments, such as, centrifugation, separation by passing the supernatant through silica gel resin, crystallization, etc.

The above examples are only used for describing technical conception and feature of the present invention, for the purpose of enabling those familiar with the art to understand and thereby implement the content of the present invention, instead of limiting the protection scope of the present invention therewith. Any equivalent changes or modifications made according to the spirit and essence of the present invention shall all be encompassed within the protection scope of the present invention.

---

What is claimed is:

1. A method for preparing rebaudioside M, the method comprising reacting rebaudioside D in a reaction solution with a glucosyl donor in the presence of recombinant cells comprising a UDP-glucosyl transferase having the amino acid sequence of SEQ ID NO: 2, to obtain rebaudioside M; wherein at least 40% of the rebaudioside D is converted to rebaudioside M after reacting for two hours.

2. The method of claim 1, wherein the glucosyl donor is UDP-glucose.

3. The method of claim 2, wherein the UDP-glucose is generated in situ from UDP and sucrose in the presence of a sucrose synthetase.

4. The method of claim 1, wherein the recombinant cells are microbial cells selected from the group consisting of: *Escherichia coli*, *Saccharomyces cerevisiae*, and *Pichia pastoris*.

5. The method of claim 1, wherein reacting rebaudioside D with the glucosyl donor in the presence of recombinant cells comprising the UDP-glucosyl transferase having the amino acid sequence of SEQ ID NO: 2, is carried out in an aqueous phase system having a temperature ranging from 25° C. to 35° C. and a pH ranging from 6.5 to 7.5.

6. The method of claim 5, wherein the aqueous phase system comprises pH 7 phosphate buffer.

7. The method of claim 5, wherein the aqueous phase system comprises a cellular permeating agent.

8. The method of claim 7, wherein the cellular permeating agent is toluene at a concentration of 1% to 3% by volume.

9. The method of claim 1, wherein the rebaudioside D is prepared by reacting rebaudioside A with a glucosyl donor in the presence of recombinant cells comprising a UDP-glucosyl transferase having the amino acid sequence of SEQ ID NO: 4.

10. The method of claim 9, wherein the glucosyl donor is UDP-glucose.

11. The method of claim 10, wherein the UDP-glucose is generated in situ from UDP and sucrose in the presence of a sucrose synthetase.

12. The method of claim 9, wherein the recombinant cells are microbial cells selected from the group consisting of: *Escherichia coli*, *Saccharomyces cerevisiae*, and *Pichia pastoris*.

13. The method of claim 9, wherein reacting rebaudioside A with the glucosyl donor in the presence of recombinant cells comprising the UDP-glucosyl transferase having the amino acid sequence of SEQ ID NO: 2, is carried out in an aqueous phase system having a temperature ranging from 25° C. to 35° C. and a pH ranging from 6.5 to 7.5.

14. The method of claim 13, wherein the aqueous phase system comprises pH 7 phosphate buffer.

15. The method of claim 13, wherein the aqueous phase system comprises a cellular permeating agent.

16. The method of claim 15, wherein the cellular permeating agent is toluene at a concentration of 1% to 3% by volume.

* * * * *